US012778396B2

(12) United States Patent
Morton et al.

(10) Patent No.: US 12,778,396 B2
(45) Date of Patent: Nov. 3, 2026

(54) ENDOSCOPE COMPRISING A SUCTION VALVE

(71) Applicant: AMBU A/S, Ballerup (DK)

(72) Inventors: Alistair David Morton, Copenhagen (DK); Anders Klüver, Ballerup (DK); Thomas Bachgaard Jensen, Værløse (DK)

(73) Assignee: AMBU A/S, Ballerup (DK)

( * ) Notice: Subject to any disclaimer, the term of this patent is extended or adjusted under 35 U.S.C. 154(b) by 118 days.

(21) Appl. No.: 18/824,157

(22) Filed: Sep. 4, 2024

(65) Prior Publication Data

US 2025/0072719 A1 Mar. 6, 2025

(30) Foreign Application Priority Data

Sep. 5, 2023 (EP) .................................... 23195488
Sep. 5, 2023 (EP) .................................... 23195491
(Continued)

(51) Int. Cl.
*A61B 1/00* (2006.01)
*A61B 1/005* (2006.01)
*A61B 1/012* (2006.01)

(52) U.S. Cl.
CPC ........ *A61B 1/0053* (2013.01); *A61B 1/00043* (2013.01); *A61B 1/00068* (2013.01);
(Continued)

(58) Field of Classification Search
CPC .... A61M 2025/091; A61M 1/91; A61M 1/75; A61M 1/774; A61M 1/00; A61B 2217/005; A61B 2017/22079
(Continued)

(56) References Cited

U.S. PATENT DOCUMENTS 3,116,905 A * 1/1964 Puster ..................... F16K 17/04 251/75
4,483,326 A 11/1984 Yamaka et al.
(Continued)

FOREIGN PATENT DOCUMENTS

AU 2016201295 A1 * 3/2016 ............ A61L 31/14
CN 216724499 U 6/2022
(Continued)

OTHER PUBLICATIONS

Search report in European Application No. 23195491.8 (1262), dated Dec. 19, 2023, 13 pages.
(Continued)

*Primary Examiner* — Anhtuan T Nguyen
*Assistant Examiner* — James Edward Boice
(74) *Attorney, Agent, or Firm* — Faegre Drinker Biddle & Reath LLP

(57) ABSTRACT

An endoscope including a handle, an insertion cord, a working channel, and a suction valve in the handle including a valve body and a stem. The valve body has a valve cylinder, an inlet connected to the working channel, and an outlet configured to be connected to a suction device. The stem is movable axially in the valve cylinder between a first position, in which the suction valve is in a valve closed state, and a second position, in which the suction valve is in a valve open state. The inlet and the outlet are connected to and extend away from the valve cylinder. The stem includes a curved flow guide. The inlet, the outlet and the curved flow guide are configured to each other to provide a curved sideways flow path through the suction valve in the valve open state.

20 Claims, 3 Drawing Sheets

(30) Foreign Application Priority Data

Feb. 28, 2024 (EP) .................................... 24160240
Aug. 29, 2024 (EP) .................................... 24197365

(52) U.S. Cl.
CPC .......... *A61B 1/00128* (2013.01); *A61B 1/005* (2013.01); *A61B 1/012* (2013.01)

(58) Field of Classification Search
USPC .................................. 600/156, 159; 604/264
See application file for complete search history.

(56) References Cited

U.S. PATENT DOCUMENTS

| | | | |
|---|---|---|---|
| 4,617,914 A | | 10/1986 | Ueda |
| 5,257,773 A | | 11/1993 | Yoshimoto et al. |
| 5,299,561 A | | 4/1994 | Yoshimoto |
| 5,322,263 A | | 6/1994 | Yoshimoto et al. |
| 5,840,015 A | | 11/1998 | Ogino |
| 5,871,441 A | | 2/1999 | Ishiguro et al. |
| 5,888,192 A | | 3/1999 | Heimberger |
| 8,273,014 B2 | | 9/2012 | Ushijima et al. |
| 8,657,801 B2 | | 2/2014 | Nielsen et al. |
| 8,827,897 B2 | | 9/2014 | Sato et al. |
| 9,480,623 B2 | | 11/2016 | Eilertsen et al. |
| 9,717,395 B2 | | 8/2017 | Toyoda |
| 11,696,748 B2 | | 7/2023 | Johnsen et al. |
| 11,937,773 B2 | | 3/2024 | Busch |
| 11,992,197 B2 | | 5/2024 | Johnsen et al. |
| 2006/0137747 A1 | * | 6/2006 | Duex .................... F16K 15/066 137/512 |
| 2007/0106204 A1 | | 5/2007 | Fedenia et al. |
| 2011/0237891 A1 | | 9/2011 | Sato et al. |
| 2012/0071843 A1 | | 3/2012 | Yamane |
| 2013/0190566 A1 | | 7/2013 | Miyoshi et al. |
| 2014/0039266 A1 | | 2/2014 | Porat |
| 2015/0122353 A1 | * | 5/2015 | Chiba .................... F04B 23/02 137/535 |
| 2018/0361034 A1 | | 12/2018 | Tobien |
| 2019/0350440 A1 | * | 11/2019 | Leong .................. A61B 1/0052 |
| 2020/0018414 A1 | * | 1/2020 | Lee .................... G05D 16/2095 |
| 2020/0359879 A1 | | 11/2020 | Cahill et al. |
| 2023/0157523 A1 | | 5/2023 | Teatini et al. |
| 2023/0157527 A1 | | 5/2023 | Morton et al. |
| 2023/0165442 A1 | | 6/2023 | Buch et al. |
| 2023/0200632 A1 | | 6/2023 | Yeh et al. |
| 2023/0277047 A1 | | 9/2023 | Silbermann et al. |
| 2023/0404377 A1 | | 12/2023 | Busch et al. |
| 2024/0324861 A1 | | 10/2024 | Jensen et al. |

FOREIGN PATENT DOCUMENTS

| | | | | | |
|---|---|---|---|---|---|
| CN | 217013962 U | | 7/2022 | |
| CN | 217040073 U | | 7/2022 | |
| CN | 115486795 A | | 12/2022 | |
| DE | 19610312 B4 | | 8/2004 | |
| EP | 0056234 B1 | | 1/1985 | |
| EP | 2433550 A1 | | 3/2012 | |
| EP | 2359741 B1 | | 9/2018 | |
| EP | 3854291 A1 | | 7/2021 | |
| EP | 3854292 A1 | | 7/2021 | |
| EP | 3903661 A1 | * | 11/2021 | ............... A61B 1/31 |
| EP | 3417906 B1 | | 3/2022 | |
| EP | 4483778 A1 | | 1/2025 | |
| JP | H05293076 A | | 11/1993 | |
| JP | H0670880 A | | 3/1994 | |
| JP | H07349 A | | 1/1995 | |
| JP | H1156770 A | | 3/1999 | |
| JP | 5161529 B2 | | 3/2013 | |
| JP | 5552014 B2 | | 7/2014 | |
| JP | 2018164565 A | | 10/2018 | |
| JP | 2023051891 A | | 4/2023 | |
| WO | 2012024413 A1 | | 2/2012 | |
| WO | 2019070998 A1 | | 4/2019 | |
| WO | 2020223427 A1 | | 11/2020 | |
| WO | 2022062513 A1 | | 3/2022 | |
| WO | WO-2022152674 A1 | * | 7/2022 | ......... A61B 1/00068 |
| WO | 2022218932 A1 | | 10/2022 | |
| WO | 2023031814 A1 | | 3/2023 | |
| WO | 2023052243 A1 | | 4/2023 | |
| WO | 2023/071852 A1 | | 5/2023 | |
| WO | 2023/071853 A1 | | 5/2023 | |

OTHER PUBLICATIONS

Search report in European Application No. 23195488.4 (1263), dated Dec. 22, 2023, 12 pages.
Search report in European Application No. 24160240.8 (1270), dated Aug. 21, 2024, 9 pages.

* cited by examiner

ENDOSCOPE COMPRISING A SUCTION VALVE

CROSS-REFERENCE TO RELATED APPLICATIONS

This application claims priority from and the benefit of European Patent Application No. 23 195 488.4 and European Patent Application No. 23 195 491.8, both filed Sep. 5, 2023, European Patent Application No. 24 160 240.8, filed Feb. 28, 2024, and European Patent Application No. 24 197 365.0, filed Aug. 29, 2024; the disclosures of said applications are incorporated by reference herein in their entirety.

TECHNICAL FIELD

The present disclosure relates to an endoscope comprising a suction valve mounted on the endoscope's handle. The present disclosure further relates to a method of assembling the suction valve of the endoscope.

BACKGROUND

Endoscopes, including specialized instruments such as bronchoscopes, arthroscopes, colonoscopes, laparoscopes, gastroscopes, and duodenoscopes, are well-known and are typically used for visual examination and diagnosis of hollow organs and body cavities, as well as to assist in surgery, e.g. for a targeted tissue sampling. Both reusable and disposable endoscopes are known. Single-use endoscopes mitigate or eliminate the risk for cross-contamination and improve availability of such instruments where and when they are needed in addition to eliminating the time and cost involved to clean re-usable endoscopes. To reduced cost, single-use endoscopes are often made with a relatively high polymer content and are assembled using adhesives.

When examining an object such as a body cavity or hollow organ with an endoscope, it is desirable to have a clear and good view or visibility of the examined object. However, the visibility of such an object is often affected by undesirable fluid or mucus, which may obstruct visibility of the object to be examined. Furthermore, it may be desirable to remove tissue parts or particles during the surgery, for example to extract a sample for further analysis, or to provide better visibility. It is thus desirable to remove such undesirable fluid or mucus, as well as such tissue parts or particles, using a suction device, such as a vacuum pump. A surgeon can start and interrupt suction by actuating a vacuum pump providing the suction. However, actuation of the pump to control suction results in considerable delays caused by starting and stopping of the pump's motor and potentially longer fluid flows since the pump is not located adjacent the handle.

To overcome these disadvantages, suction valves comprising housings and pistons movable within the housings can switch the vacuum on and off without shutting off the vacuum pump. However, with these suction valves fluid, mucus and tissue sucked-off by the suction device is sharply deflected several times within the suction valve, which considerably reduces the volume flow, increases the load on the vacuum pump, and reduces the pumping capacity and suction performance. Furthermore, narrowing of the valve increases the risk of clogging, which leads to interruptions in the medical procedure, potentially endangering a patient's safety. Additionally, known suction valves are complex, with a large number of parts, which makes the valves expensive to manufacture, which is of considerable disadvantage, especially for the use of such a suction valve with a single-use endoscope.

Furthermore, studies have shown that the carbon footprint of maintaining and cleaning re-usable endoscopes may be equal to or greater than the carbon footprint of single-use endoscopes. However, it is important to continue reducing the carbon footprint of single-use devices. Designing single-use devices with lower carbon footprint materials comes with drawbacks, however, since such materials may have different characteristics in a range of variables including temperature, adhesion, shrinking, warpage, rigidity, and strength.

BRIEF DESCRIPTION OF THE DISCLOSURE

The object of the present disclosure is therefore to overcome or at least reduce the disadvantages of the related art. More specifically, it is the purpose of the present disclosure to provide an endoscope having a suction valve, wherein the suction valve provides an appropriate flow rate in an open state of the suction valve, reduces a risk of clogging, and is inexpensive and easy to manufacture.

It is also an object of the present disclosure to provide a single-use endoscope with even lower carbon footprint than prior single-use endoscopes. The carbon footprint may be reduced by selecting lower carbon footprint materials and reducing the use of adhesives to bond plastic components. Synergistically, by configuring components in novel ways the reduction of the carbon footprint may result in lower material and assembly costs.

In one aspect, the present disclosure provides an endoscope comprising a suction valve mounted on the endoscope's handle. In a second aspect, the present disclosure provides a method of assembling the suction valve of the endoscope. In a third aspect, the present disclosure provides a visualization system including the endoscope according to the first aspect.

In one embodiment according to the first aspect, the endoscope comprises a valve comprising a valve cylinder, an inlet, an outlet, and a stem. The inlet and the outlet are connected to, and extending away from, the valve cylinder. The stem comprises a curved flow guide.

The suction valve may further comprise a valve body having the valve cylinder, the inlet connected to the working channel, and the outlet provided and configured to be connected to a suction device. The stem is movable axially in the valve cylinder between at least a first position, in which the suction valve is in the valve closed state, and a second position, in which the suction valve is in the valve open state.

Preferably, the handle comprises a curved flow path provided by an enclosed angle between a first orientation, or center axis, of the inlet and a second orientation, or center axis, of the outlet, being larger than 90° and smaller than 180° seen in a sectional side view of the handle in an assembled state of the suction valve, in combination with the curved flow guide of the stem. The curved flow guide may be configured to guide the fluid and the mucus from the inlet to the outlet in the valve open state of the suction valve.

The endoscope may comprise a handle or interface and a working channel configured to let fluid and mucus sucked from the patient's body cavity flow therethrough. The suction valve in the handle is configured to control suction through the working channel and has a valve closed state and a valve open state.

The interface may be formed on, or substitute for, the handle. The handle or interface may contain control elements, such as a lever or wheel for controlling bending of the bending section, and ports for accessories, such as a video processing apparatus or the suction device. The suction device may be a vacuum pump. The handle is preferably designed in such a way that it can be ergonomically gripped and operated by the user or operator or surgeon with just one hand. This means that all important operating elements on the handle or interface are preferably arranged in such a way that the user can operate them with one hand without having to change a position of his/her hand. The handle may comprise a shell. Preferably, the shell is made from a plastic material. Furthermore, the shell preferably comprises two half shells. The interface may be prepared or provided to be connectable to a robotic arm.

Handles, and other components of single-use endoscopes, are typically manufactured from acrylonitrile butadiene styrene (ABS). ABS is an amorphous polymer suitable for applications that require high strength, stiffness, and heat resistance, while polypropylene (PP), a semi-crystalline polymer, is more suitable for applications that require high flexibility. For example, the elongation at break of ABS is about 30% while the elongation at break of PP may be about 100%. Further, ABS requires more heat to maintain the polymer at a high level while feeding the material to an injection molding machine. Otherwise, the material will cool quickly which can result in structural flaws in the final product. And ABS, due to being amorphous, does not lend itself well to on-the-fly processing changes during manufacturing, which changes result in more scrapped material relative to PP. In sum, an endoscope according to the present disclosure reduces carbon footprint by using PP instead of ABS and provides novel features especially configured to solve the problems caused by such substitution, including lower rigidity and lower adhesion characteristics. The carbon footprint can be reduced further by using bio-PP instead of carbon based PP.

The endoscope may comprise an insertion cord extending from the handle or interface. The insertion cord may have an insertion tube, a bending section, and a distal tip unit formed at the distal end of the insertion cord. The distal tip unit may comprise an image capturing means, like a camera, and a light emitting device, like a light emitting diode (LED).

Preferably, the endoscope is a single use endoscope.

The working channel is provided and configured to transport fluid, mucus and tissue parts or particles from the patient's body cavity. Furthermore, the working channel may be configured to guide a surgical tool or instrument through it to a surgical location in the patient's body. For this purpose, the working channel may have a Y-connector in the handle that allows insertion of the surgical tool or instrument into the working channel.

The valve body, which may also be designated as a valve housing, may be formed cylindrically at least in portions and may thus be described as including a valve cylinder that extends in an axial direction of the suction valve.

The inlet and the outlet of the suction valve are preferably formed as integral parts or portions of the valve body. Thus, the valve body may comprise a single part including the inlet and the outlet. The inlet and the outlet may have a geometry of a pipe section, preferably of a pipe section with an annular cross-section.

The inlet and outlet may extend away from an outer cylindrical surface of the valve cylinder of the valve body, preferably straight or linear. The orientation or center axis of the inlet seen in a sectional side view of the handle in an assembled state of the suction valve may extend away from the outer cylindrical surface of the valve cylinder both in a radial and in an axial direction of the valve cylinder. The orientation or center axis of the outlet seen in a sectional side view of the handle in an assembled state of the suction valve may extend away from the outer cylindrical surface of the valve cylinder both in a radial and in an axial direction. It is also conceivable that the inlet or the outlet extends away purely radially from the valve cylinder, i.e. does not extend axially in the axial direction of the valve cylinder.

The inlet has thus preferably the first center axis or orientation. The first center axis is a virtual auxiliary axis and extends from a center position of the inlet in the direction of the extension of the inlet seen in a sectional side view of the handle in the assembled state of the suction valve. The inlet is provided and configured to be connected to the working channel. The inlet may be connected directly to the working channel. Alternatively, the inlet can be connected to the working channel via a suction channel, especially preferably to the Y-connector of the working channel. The working channel may at least partly be provided by the working channel tube. The suction channel may e.g. be configured as a separate hose or tube.

The outlet has preferably the second center axis or orientation. The second center axis is a virtual auxiliary axis and extends from a center position of the outlet in the direction of the extension of the outlet seen in a sectional side view of the handle in the assembled state of the suction valve. The outlet is provided and configured to be connected to the suction device. The outlet may be connected directly to the suction device. Alternatively, a hose may be provided between the outlet and the suction device. Alternatively or additionally, at least one coupling element and/or at least one deflector element and/or at least one pipe element may be provided between the outlet and the suction device.

The stem is arranged in the valve body in such a way that the stem is able to move in the axial direction of the suction valve in the valve body, especially in the valve cylinder of the valve body. The axial movement, at least in one direction, can be caused by pushing a button. The button may be a button portion which is preferably formed integrally with a remainder of the stem at an end portion of the stem. Alternatively, the button may be a button element attached to the stem, in particular to the end portion of the stem, which is positioned outside of the valve body at least in the closed state of the valve. The button portion or element may protrude axially from the valve body, so that a user can press the button portion or element in order to move the stem axially in the valve body. The stem may be moved in the valve body in such a way that it shifts the suction valve at least between the valve closed state of the suction valve in its first position and the valve open state of the suction valve in its second position. The stem may be configured to seal between an inlet opening and an outlet opening in the suction valve closed state, and the stem may be configured to enable a fluid flow between the inlet opening and the outlet opening of the valve body in the suction valve open state. The suction valve may be configured to manually control the suction through the working channel, in particular by the user pressing the button towards the housing of the endoscope. In this way, the user can easily control the suction valve and can switch between the valve closed state and the valve open state.

The suction valve, in particular the parts thereof, may be made of a plastic material or polymer. Especially preferred, the suction valve, in particular parts thereof, preferably the valve body and the stem, may be manufactured in an injection molding process, i.e. may be injection molded parts. The suction valve may comprise at least 70% polypropylene polymer, or may consist essentially of polypropylene polymer.

The enclosed angle between the first center axis of the inlet and the second center axis of the outlet is preferably larger than 90° and smaller than 180°, in order to provide—together with the curved flow guide of the stem—the curved sideways flow path. Preferably, the enclosed angle is larger than 100°. Especially preferred, the enclosed angle is larger than 110°. Preferably, the enclosed angle is smaller than 170°. In a particularly preferred embodiment, the enclosed angle is approximately 120°.

It is to be understood that in the formulations "larger than" and "smaller than", the limit value itself is not part of the claimed range of values in each case.

Further, the stem comprises the curved flow guide. The curved flow guide is a section with a curved surface, which is part of the stem or mounted to the stem. Preferably, the curved flow guide has exactly one curved surface to guide the fluid and mucus and is free of edges and/or discontinuities. Preferably, the curved flow guide is formed integrally with the stem, i.e. is an integral part or portion of the stem.

Providing such a suction valve in an endoscope can ensure that the fluid and mucus passing through the suction valve in the valve open state of the suction valve is deflected as little as possible and thus a suitable flow through the suction valve can be achieved. Such flow advantageously reduces or even prevents blockages in the suction valve, which would disrupt a surgical procedure. Furthermore, the reduced number of components means that the assembly effort and thus the costs of the suction valve are reduced considerably, which is particularly important for a single-use endoscope. To improve the flow through the valve, the stem is provided with a curved flow guide which in the pressed or opened state of the valve, i.e. the valve open state, smoothly guides the flow through the stem and prevents the chicane-like obstruction and flow of the known suction valves. In other words, the curved flow guide, in particular the curved surface, is designed such that it provides a curved, continuous transition between the inlet and the outlet in the valve open state.

In one aspect, the curved flow guide may comprise at least a first, preferably infinitesimally small, surface or portion tangential to, i.e. parallel to a direction of the first center axis or orientation of the inlet and a second (infinitesimally small) surface portion tangential to, i.e. parallel to a direction of the second center axis or orientation of the outlet.

In other words, a curvature of the curved flow guide may be configured such that the flow guide at a first end portion facing the inlet is oriented substantially in the direction or a direction parallel to the first center axis, and at a second end portion facing the outlet is oriented substantially in a direction or a direction parallel to the second center axis.

Preferably, a curvature characteristic does not change in the curved surface or the curved flow guide, i.e. there is no inflection point, where the curvature changes sign. Particularly preferably, the curvature or a radius of the curved flow guide is constant between the first end portion and the second end portion, so that there is provided a continuous transition between the inlet and the outlet. Such a design of the curved flow guide can make the redirection of the flow of the fluid and the tissue even more uniform and with less resistance.

The valve body of the suction valve may comprise a valve seat configured to make circumferential contact with a sealing edge of the stem in the valve closed state of the suction valve, to thereby block the flow of fluid and mucus from the inlet to the outlet. The valve seat may be inclined with respect to the axial direction and the radial direction of the suction valve or valve cylinder or stem. The valve seat may comprise a conical engagement surface, which sealingly engages with a conical engagement surface of the stem in the valve closed state.

The valve seat may be formed on the valve body or may be formed as a portion of the valve body. Preferably, the valve seat and the valve body are formed in one piece. Particularly preferably, the valve seat is formed integrally with the valve cylinder, which is a cylindrical part or portion of the valve body.

The sealing edge may be formed on the stem or may be formed as a portion of the stem. Preferably, the remainder of the stem and the sealing edge are formed in one piece. The valve seat surrounds or forms a passage opening between the inlet and the outlet. In the closed state of the suction valve, i.e. in the valve closed state, the sealing edge of the stem is in contact with the valve seat and the passage through the suction valve is blocked. The valve seat may be oriented both at an angle to the axial direction of the valve cylinder and at an angle to the radial direction of the valve cylinder. By angling the valve seat in this way, the flow through the suction valve can be further improved and installation space of the suction valve in the handle can be reduced at the same time.

The valve seat of the valve body and the sealing edge of the stem may be tapered outwards at a pointed or acute angle in order to form a substantially conical sealing seat.

The sealing seat may be designed as a conical sealing seat, which does not require additional seals, such as an O-ring. The valve seat and the sealing edge may be tapered in one direction towards the button element or portion. Preferably, the taper can be about 19°.

The valve may be devoid of an O-ring or rubber or silicone material between the valve stem and the valve seat. The sealing may be achieved purely from stem-to-valve seat contact, which are made from plastic, preferably from polypropylene, as this can be sourced from sustainable biobased plastics. Omitting an O-ring from the flow path further improves the flow performance through the suction valve.

To improve the sealing performance of the plastic-to-plastic sealing, the stem and the valve seat may be conical in shape which increases the sealing force compared to a simple flat perpendicular sealing surface interface. The stem and valve seat may be tapered outwards at a 19° angle relative to the longitudinal axis of the stem. The angle need not be 19° exactly. Such a design can further reduce the number of components and the assembly effort and thus the cost of the suction valve, since the additional sealing element can be omitted.

The stem may comprise a sealing plate. The sealing plate may be formed at an end portion of the stem away from the button portion or element. The sealing plate may have the sealing edge on an outer edge surrounding the sealing plate i.e. a peripheral or circumferential edge.

The sealing plate may form an end portion of the stem. The sealing plate may include the sealing edge. In the closed state of the suction valve, i.e. in the valve closed state, the sealing plate can completely close the passage in the valve seat, taking up little installation space. Furthermore, the plate-shaped geometry of the sealing plate allows the longest possible travel of the stem and thus a large opening cross-section.

The stem may comprise a retention hook. The retention hook may be provided at the sealing plate of the stem in a direction facing away from the button portion or element of the stem.

The retention hook or at least a portion of the retention hook may extend in a radially outward direction beyond the sealing plate.

The retention hook may be an integral portion, formed in one piece with, the stem.

The retention hook may be formed as a barb in the stem. The retention hook may be resiliently formed on the sealing plate so that the stem can be easily pushed through the valve seat in an assembly direction. In a disassembly direction directly opposite to the assembly direction, the retention hook hooks onto the valve seat and prevents the stem from being pulled out of the valve body. The retention hook may preferably be V-shaped.

The valve seat of the valve body may be made of an elastic material or is elastically mounted. The elastic valve seat allows the stem to be mounted into the valve body in a push-through manner.

The valve seat may be formed as a resilient member that is elastically deformable in a radial outward direction to allow an object with a slightly larger diameter than the diameter of the valve seat to pass through the valve seat, and the valve seat resiliently returns to its original shape after the object has passed through.

Such a configuration of the valve seat allows the suction valve to be assembled in a simple manner. Specifically, the suction valve may be assembled by inserting or sliding the stem into the valve body, which significantly reduces the assembly effort of the suction valve and thus the costs of the suction valve. Further, the valve body and stem may be at least largely formed in one piece, which reduces manufacturing costs and assembly costs. Similarly, the retention hook may be formed as an elastically resilient part, which can be compressed during insertion into the valve cylinder during assembly, and “spring” out i.e. decompress after passing the valve seat.

The suction valve may comprise a valve spring. The valve spring may be provided between the valve body and the stem, in order to force and to hold the suction valve in the closed state. The valve spring may have at least one bypass hole, which, in the state when the suction valve is closed, i.e. in the valve closed state, allows ambient air to be drawn through the valve. The valve spring may be a part separate from the stem or the valve body. Alternatively, the spring may be a preferably elastic integral part of either the valve body or the stem. It is added that the spring must not be necessarily provided. In particular, the stem can be manually moved between at least the first position and the second position without being preloaded by a spring towards one of the positions.

The valve spring may radially surround at least one area or portion between the button element or portion and the valve body. However, embodiments are also conceivable in which the valve spring is formed in the button and/or in the stem and/or in a surrounding sleeve. The valve spring can be made of an elastic material, preferably rubber.

The spring may include at least the one, preferably two bypass holes. By forming the bypass holes, damage to the vacuum device and/or the endoscope can be prevented in the valve closed state. The rubber valve spring makes the suction valve easy to install, since the valve spring can be mounted on the stem and the valve body without tools. Furthermore, the valve spring in such a design can protect the suction valve in such a way that contamination is prevented from entering a gap between the stem and the valve body.

Preferably, the valve spring may be installed in the suction valve in such a way that the valve spring is preloaded. In other words, the valve spring may be installed in the suction valve in a slightly compressed state, so that in a state in which no activation force acts on the suction valve from the outside, e.g. from the operator, the valve spring presses the sealing edge of the stem into the valve seat with the pretensioning force and thus increases the tightness of the suction valve.

The valve spring may be configured to form a bellows shape in a compressed state of the valve spring, thereby closing the bypass hole(s). In other words, the valve spring may form at least one fold in a compressed state of the spring so that the bypass hole is closed by the spring itself. By configuring the spring in this way, the number of components for the suction valve can be further reduced.

The stem may comprise a stop, which may be configured to be brought into contact with the valve body and prevent overpressing of the suction valve. The stop, preferably in the form of at least one rib, may extend in a radial direction of the stem. If the button is pressed too hard, the stop comes into contact with the valve body, so that the stem cannot be pressed further into the valve body. Further, the stop may ensure that the stem and the flow guide are positioned in a pre-configured position for optimum flow in the suction valve.

Due to the integral design of the stop with the stem, the number of components of the suction valve can be further reduced, which further reduces the assembly effort and thus the assembly costs of the suction valve. Fewer components also reduces the amount of adhesive that is used to bond components of the endoscope to each other, further reducing the carbon footprint.

The stem may comprise a recess. The recess may extend, at least in sections, normal or perpendicular to the axial direction of the stem, wherein the recess, in the open state of the suction valve, connects the input and the output to each other and wherein the recess comprises the curved flow guide of the stem.

The recess may be formed on or in the stem in order to connect the inlet to the outlet in the opened state of the suction valve. The recess may be configured in such a way that at least a part of the recess is formed perpendicular to the axial extension of the stem. The recess may preferably be formed as a through hole passing through the stem. Alternatively, the recess may be a recess located on a side of the stem. The curved flow guide may be formed in or on the recess. In other words, a surface or section of the stem bounding the recess may be formed as the curved flow guide.

With such a recess in or on the stem, the suction valve can be designed to be more compact and the volume flow through the suction valve can be increased.

The valve body and the stem may each be formed in one piece from a plastic material, preferably polypropylene. The valve body and/or the stem are preferably made from a thermoplastic polymer, e.g. polypropylene, especially biodegradable polypropylene, polystyrene (PS), polycarbonate (PC), acrylonitrile butadiene styrene, polyoxymethylene (POM), etc. However, also other polymer materials or other materials are conceivable. However, polypropylene is preferred because it reduces the carbon footprint relative to many other polymers, such as PS, PC and ABS.

Bio-based PP is understood to originate from biomass, which is renewable, e.g., within a time span of up to 10 years or up to 50 years. This is opposed to so-called synthetic PP which is made from a fossil-based feedstock, such as crude oil, which is not renewable, at least not when considering a time span of up to e.g., a thousand years. One way to establish whether the PP is bio-based or based on a fossil feedstock, is by a carbon 14 analysis. A carbon 14 analysis can also provide an estimate of the relationship between the content of bio-based PP and the content of fossil-based PP. Bio-based polypropylene may be manufactured from natural materials such as lignocellulosic biomass (starch and cellulose), fatty acids, and organic waste, e.g., food waste or waste products from farming or forestry. Also, corn, sugar cane, vegetable oil, and some other types of biomass may be applied. One practical way to add bio-based PP as a fraction of the handle shell material is to apply the so-called bio-attributed concept, where the bio-based fraction of the PP is calculated from the mass balance approach (or model). This means that the fraction of bio-based PP in a component may not be known, but the average fraction over some time, or for a certain number of said components, is well known. The supplier of the PP raw material to the molding, will comply with the relevant standards (such as the series of ISO 16620 standards: ISO 16620-1:2015, ISO 16620-2:2019, ISO 16620-3:2015, ISO 16620-4:2016, ISO 16620-5:2017) related to the mass balance model. Applying this approach means that in order to know the bio-based fraction of PP in a specific component, or a specific batch of component, an analysis, such as an analysis of the carbon-14 content, may be necessary. The rest of the PP may come from fossil resources. Some of the PP could also be based on recycled PP.

Some changes in the design of the endoscope have been found to simplify the manufacturing of the endoscope and have enabled a shift from previous used polymers, such as ABS, into the use of PP, including bio-based PP. Recycled PP may comprise a combination of bio-based PP and fossil-based PP. As more and more bio-based PP is applied, the fraction of bio-based PP in recycled PP will increase. The content of bio-based PP does not influence the use of additives which may be added to the PP in order to provide specific, e.g., mechanical, characteristics to the endoscope material. The PP of the components may comprise at least 20% bio-based PP, alternatively, at least 40% bio-based polypropylene. The fraction of bio-based PP may also be at least 60%, or at least 80%. A higher fraction of bio-based PP means that the carbon dioxide emissions related to the endoscope during their life cycle will be lower. Some endoscope components, such as the valve and handle housing shells, may consist essentially of PP. Processing additives may be added as is known in the art. Alternatively, the components may comprise at least 60% PP, preferably more than 70% PP, of which at least 20% is bio-based PP. Fibers, such as natural fibers, may be added to modify physical properties, such as strength.

The suction valve may be compatible with working channel inner diameters of 1.2 mm to 3.8 mm, meaning that a sphere of diameter 3.8 mm or larger is preferably able to pass through the suction valve in its activated position, i.e. in the valve open state. In other words, the recess in the stem may have a cross-sectional area of at least 3.8 mm.

The suction valve may further comprise a valve end cap, which preferably is ultrasonically welded to the valve body, which avoids gluing, which may be a labor-intensive process. In an alternative embodiment, the valve end cap may be made in one piece with the valve body. However, embodiments in which the cap is glued to the valve body are also conceivable. This is particularly conceivable if the material of the valve body is not polypropylene.

The valve body may be provided with a guide slot or groove for guiding a corresponding pin of the stem to ensure a straight up and down or axial movement of the stem in the valve body or the valve cylinder of the valve body when actuating the suction valve.

The valve spring may feature preferably small bumps for sealing against the valve body.

The valve spring also may act as the movement stop for the stem displacement i.e. when the spring is fully compressed it may act as a stop and may feature bump stops.

The inlet and the outlet may be arranged at an angle smaller than 180° to each other in a top view, that is, in a viewing direction that corresponds to the axial direction of the valve body and the stem.

In an embodiment according to the second aspect, a method of assembling the suction valve of the endoscope as described above is provided. The suction valve comprises a valve body, a stem and a valve spring, the valve body having an elastic valve seat. The method comprises: attaching the valve spring to the stem; pushing the stem into the valve body; elastic bending of the valve seat of the valve body with the stem; and positioning the valve spring on the valve body.

The valve spring may be attached to the stem in such a way that a clamping edge of the valve spring is elastically pulled on and the clamping edge is inserted into a receiving groove formed on the stem.

The stem may be inserted into the valve body through an opening in the valve body. The insertion takes place in an actuation direction of the stem, that is, in a direction in which the stem is movable within the valve body of the suction valve.

The stem may elastically bend the valve seat, which is located inside the valve body, preferably radially outward. In other words, the stem widens the valve seat to such an extent that the stem or a section of the stem, preferably the section of the stem that has the sealing edge, can be pushed through or passes the valve seat. When the section of stem has passed the valve seat, the valve seat snaps back into its predetermined shape.

The valve spring or a section of the valve spring may be pulled over the valve body so that the valve spring is fixed to the valve body. For this purpose, the valve spring can be elastically expanded and then it shrinks back on the valve body.

Such a method allows the suction valve to be assembled without any tools, which reduces the assembly effort and thus the manufacturing costs of the suction valve.

The stem may comprise a retention hook, in which case the method may further comprise, after pushing the stem into the valve body, passing a retention hook of the stem through the valve seat. In other words, the stem may further comprise the retention hook, which is preferably formed on a portion of the stem that is first inserted into the valve body. The retention hook is elastically mounted on the stem and acts as a barb that prevents the stem from being pulled out of the valve body once the retention hook has passed the valve seat. The retention hook ensures that the suction valve does not disassemble itself even in the event of incorrect operation or rough handling.

The valve may be assembled by attaching the valve spring to the stem and pushing the stem into the valve body until a bottom of the stem including the retention hook is past the valve seat. The valve seat is somewhat flexible and flexes when the stem is pushed through. The retention hook is compressed as the stem is pushed through the valve body and through the valve seat after which it then expands creating a backup hard stop preventing the stem from being pulled back past the valve seat. The engagement of the sealing edge of the stem and the valve seat in itself prevent the stem from being pulled past the valve seat in a first step, before the retention hook takes effect. The valve spring is positioned on the valve body.

The stem may comprise a guide pin and the valve body may comprise a guide slot or groove, in which case the method may comprise inserting the guide pin of the stem in the guide slot, preferably directly before, or at the same time as pushing the stem into the valve body.

In an embodiment according to the third aspect, a visualization system comprises the endoscope according to the first aspect or made according to the second aspect, and a video processing apparatus (VPA) couplable to the endoscope and capable of outputting a live image recorded by the camera e.g. an image sensor of the endoscope, on a display. The video processing apparatus may comprise a built-in display and/or a detachable display and/or may be couplable to an external display. The video processing apparatus may be a video processing apparatus showing an image or a video captured by an image capturing means arranged at the distal tip unit.

In a fourth aspect, the present disclosure relates to a system comprising the endoscope according to the first aspect, including all variations thereof, wherein the system further comprises a suction device that is connectable directly or indirectly, for example through a hose, to the outlet of the valve body of the suction valve. The suction device may be a vacuum pump or the like. The suction device may be directly coupled to the endoscope or be part of, or be incorporated with, the endoscope.

BRIEF DESCRIPTION OF THE DRAWINGS

The disclosure is explained in more detail below using preferred embodiments and referring to the accompanying figures.

The figures are schematic in nature and serve only to understand the disclosure. The features of the different embodiments can be interchanged among each other.

DETAILED DESCRIPTION

Figure 1:
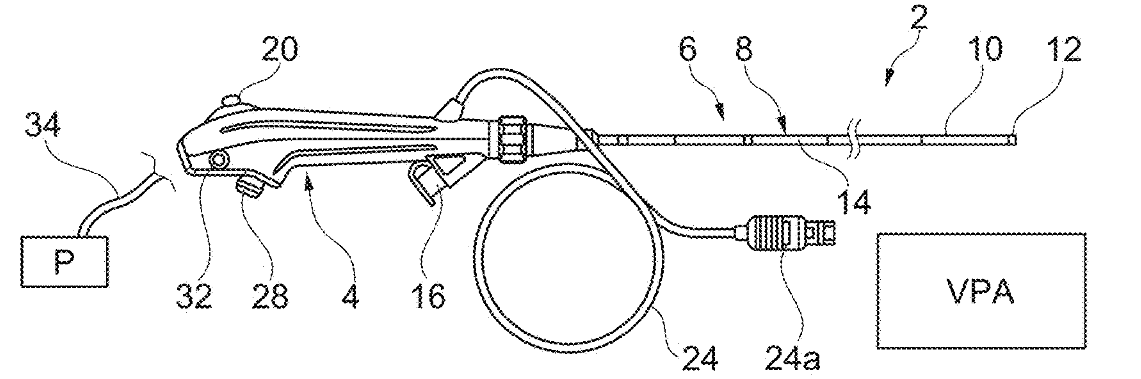
FIG. 1 shows a side view of an endoscope according to the present disclosure, a video processing apparatus and a suction device.

FIG. 1 shows a side view of an endoscope 2 according to the present disclosure, which is preferably a single-use endoscope. The endoscope 2 comprises a handle 4 and an insertion cord 6 extending distally from the handle 4. The insertion cord 6 is configured to be inserted into a patient's body and comprises an insertion tube 8, a bending section 10 and a distal tip unit 12. The endoscope 2 further comprises a working channel 14 which extends from a biopsy port or a working channel access port 16 provided at the handle 4 to the distal tip unit 12. The working channel 14 is comprised by a working channel tube 18 (shown in FIG. 2) arranged inside the handle 4, the insertion tube 8, and the bending section 10. The handle 4 comprises a steering actuator 20, formed as a lever or wheel, for bending the bending section 10 of the insertion cord 6. The working channel tube 18 and the working channel access port 16 are connected via a Y-connector 22. The endoscope 2 is connectable to a video processing apparatus (VPA, schematically illustrated) via a connecting cable 24 comprising an electrical connector 24*a* insertable in a socket (not shown) of the video processing apparatus. Alternatively the endoscope 2 may be wirelessly connectable to the video processing apparatus, e.g. by a wireless HDMI connection.

When a surgical instrument or tool is inserted into the working channel 14, the surgical instrument or tool is inserted into the working channel access port 16 and guided through the Y-connector 22 into the working channel tube 18.

The endoscope 2 further comprises a suction valve 26, having a suction button 28 formed on the handle 4 and configured to control a suction power through the working channel 14 of the endoscope 2. The suction valve 26 is connected to a suction channel 30 and a vacuum port 32, which protrudes from or is embedded in the handle 4 (shown in FIG. 2). The endoscope 2 is connectable to a suction pump P (schematically illustrated) via a hose 34, which is connectable to the vacuum port 32 of the endoscope 2.

Figure 2:
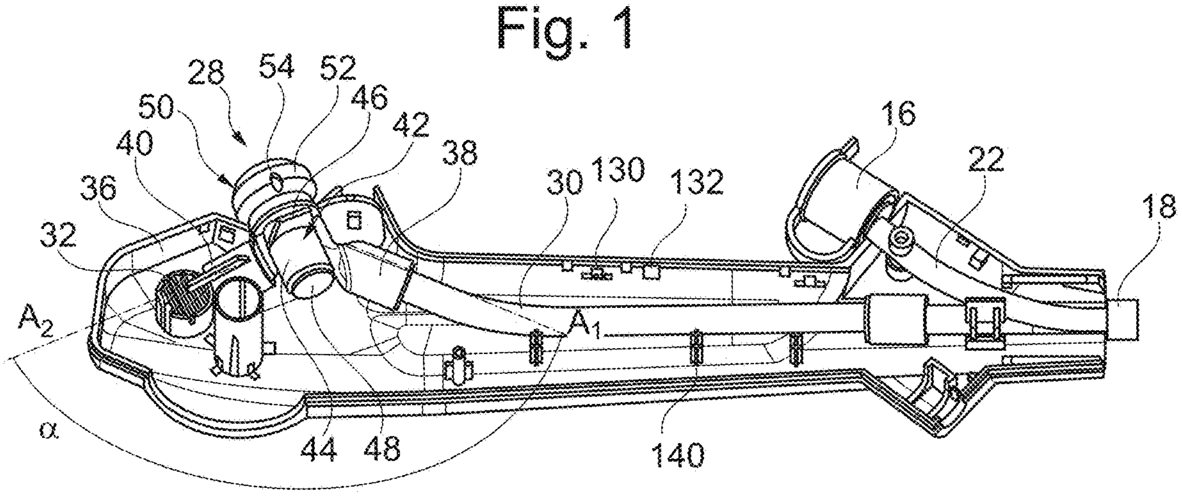
FIG. 2 shows a perspective view of a half shell of the handle having a suction valve.

FIG. 2 shows the handle 4 in an open state. The handle 4 is formed substantially from two half-shells 36 that form the housing of the handle. In FIG. 2, one of the two half-shells 36, and other elements of the endoscope 2 which are not necessary for an understanding of the present disclosure, are not shown for the sake of clarity. All other mechanical, optical and electronic components, which are formed in the handle 4 in a conventional endoscope, are or may be formed in the endoscope 2 of the present disclosure.

The two half-shells 36 are connected with snap-fit shell fasteners 130, each including a snap lug and a snap hook. The snap lug is placed on one housing shell and a corresponding snap hook is placed on the other housing shell. When the housing shells 36 are pressed together the snap hooks engage with the snap lugs to attach the housing shells to each other. In the range of 6-12 snap-fit shell fasteners provide a strong and stable connection between the housing shells. In one variation, 7-9 snap-fit shell fasteners 30' connect the two housing shells. The two half-shells 36 may also comprise press-fit component fasteners 140. A press-fit component fastener may comprise a stud or rod and a cavity. The stud can be on a handle shell and the cavity be part of a component to be attached thereto, or vice versa, preferably without adhesives. The two half-shells 36 may also comprise alignment means 132, i.e., pairs of a first alignment part and a second alignment part, may be in the range of 5-13, preferably in the range of 6-10. The combination of the snap-fit shell fasteners, press-fit component fasteners, and optionally alignment means, form a three-dimensional support network that has the effect that when the two housing shells are snapped together, they cannot be displaced relative to each other in any direction. Also, along the handle split line the connection will be firm and robust. By preventing displacement, in particular due to the use of the alignment means 132, it is also prevented that the shells will un-snap and separate. The three-dimensional network comprises a plurality of alignment means and snap-fit shell fasteners. The three-dimensional network is suitable particularly when the shells are made from relatively more flexible material, such as PP, even more particularly when a wall thickness of a shell is thin, to reduce material costs and carbon footprint. In one example, the wall thickness of more than 70% of the shell is 2.5 mm or less, preferably 2.0+/−0.2 mm. The three-dimensional support network, snap-fit shell fasteners, press-fit component fasteners, and the alignment means, are described in more detail in commonly-owned European Patent Application No. 24 160 240.8, titled "Handle for an endoscope," the disclosure of which is incorporated herein by reference in its entirety.

The suction channel 30 connects the suction valve 26, which is mounted between the two half shells 36 at a proximal end portion of the handle 4, to the Y-connector 22 and runs in a longitudinal direction of the handle 4, that is, substantially in a direction, which continues the insertion cord 6. The suction valve 26 comprises an inlet 38, which is configured to connect to the suction channel 30. The inlet 38 is configured as a receptacle that receives an end of the suction channel 30. The suction channel 30 has a tubular shape and may be in the form of an elastomeric tube or a rigid pipe. The end of the suction channel (tube) 30 may be press-fit into the receptacle of the inlet 38 to reduce or eliminate use of adhesives, particularly when the suction valve body is made from polypropylene, which is difficult to adhesively bond. The receptacle may be tapered to better secure the suction channel (tube) 30. The suction valve 26 further comprises an outlet 40, which is connectable to the vacuum port 32. The outlet 40 is configured as a connector that connects to the vacuum port 32. The outlet 40 may also be formed as a receptacle, preferably tapered, to form a press-fit connection with the vacuum port 32.

Figure 3:
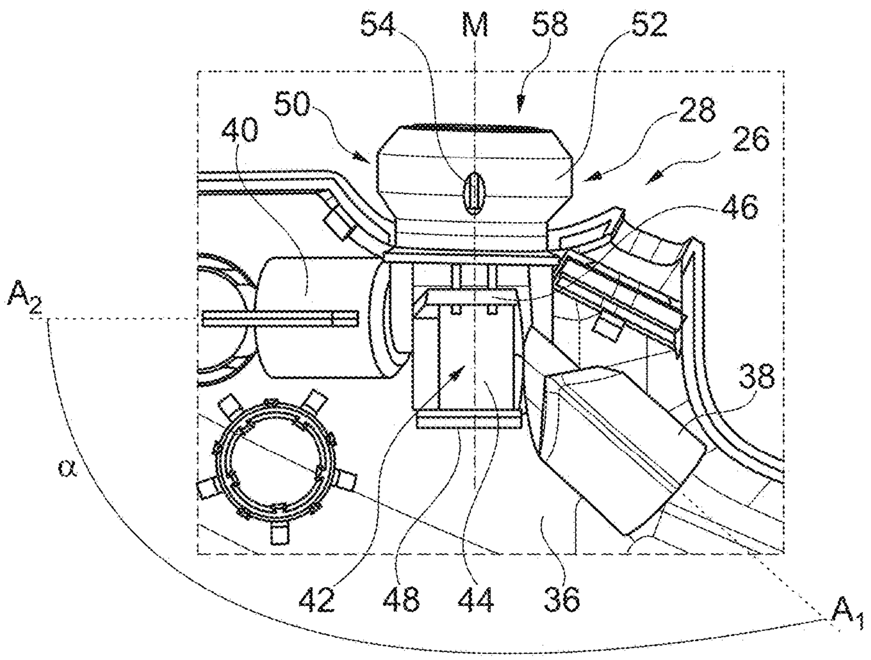
FIG. 3 shows the suction valve mounted in the half shell in an enlarged side view.

In the following, the external structure of the suction valve 26 is explained in more detail with reference to FIGS. 2 and 3. FIG. 3 is an enlarged view of the suction valve 26 in the assembled state, whereby the suction channel 30 and the vacuum port 32 are not shown in FIG. 3. Flow testing at steady state and a vacuum of −0.35 kPa relative to atmospheric pressure has show that the suction valve described herein increased flow by 19+/−1% relative to a similarly sized valve without the curved sideways flowpath described below.

The suction valve 26 comprises a valve body 42, which comprises a valve cylinder 44 extending in an axial direction of the suction valve 26. The valve body 42 further comprises the inlet 38 and the outlet 40. The inlet 38 and outlet 40 each have a substantially tubular geometry with a substantially circular cross-sectional configuration. Seen in the side view of the handle in an assembled state of the suction valve in FIG. 3, the inlet 38 has a first center axis A1 and the outlet 40 has a second center axis A2. The first center axis A1 extends in a center position of the inlet 38 in a direction of extension of the inlet 38. The second center axis A2 extends in a center position of the outlet 40 in a direction of extension of the outlet 40. A first angle $\alpha$ is enclosed between the first center axis A1 and the second center axis A2. The first angle $\alpha$ is greater than 90° and less than 180°. Preferably, the angle is greater than 110°. Particularly preferably, the angle is about 120°.

The valve body 42 is formed in one piece from a plastic material, preferably polypropylene. Further the valve body 42 comprises fixing projections 46 formed thereon, which are configured to fix the suction valve 26 in the handle 4 between the half-shells 36.

The suction valve 26 further includes an end cap 48 formed on an end portion of the valve cylinder 44 facing an interior of the handle 4, and closing the valve cylinder 44. Specifically, the end cap 48 closes a substantially circular bottom opening of the valve body 42. The end cap 48 and the valve body 42 are welded together. Alternatively, it is conceivable that the end cap 48 may be fixed in place by adhesive bonding or by a latching action.

A valve spring 50 is formed on an end portion of the valve cylinder 44 opposite the end cap 48. The valve spring 50 protrudes for the most part from the handle 4 and ensures that the suction valve 26 is maintained in an initial valve closed state or is returned to the initial valve closed state without a user actuation. The specific operation of the valve spring 50 will be explained in more detail below with reference to FIGS. 4 and 5. A bypass hole 54 is formed in a side surface 52 of the valve spring 50. The bypass hole 54 allows ambient air to be drawn through the suction valve 26 into the outlet 40 in a closed state of the suction valve, that is, in a state in which the volume flow from inlet 38 to outlet 40 is blocked.

Figure 4:
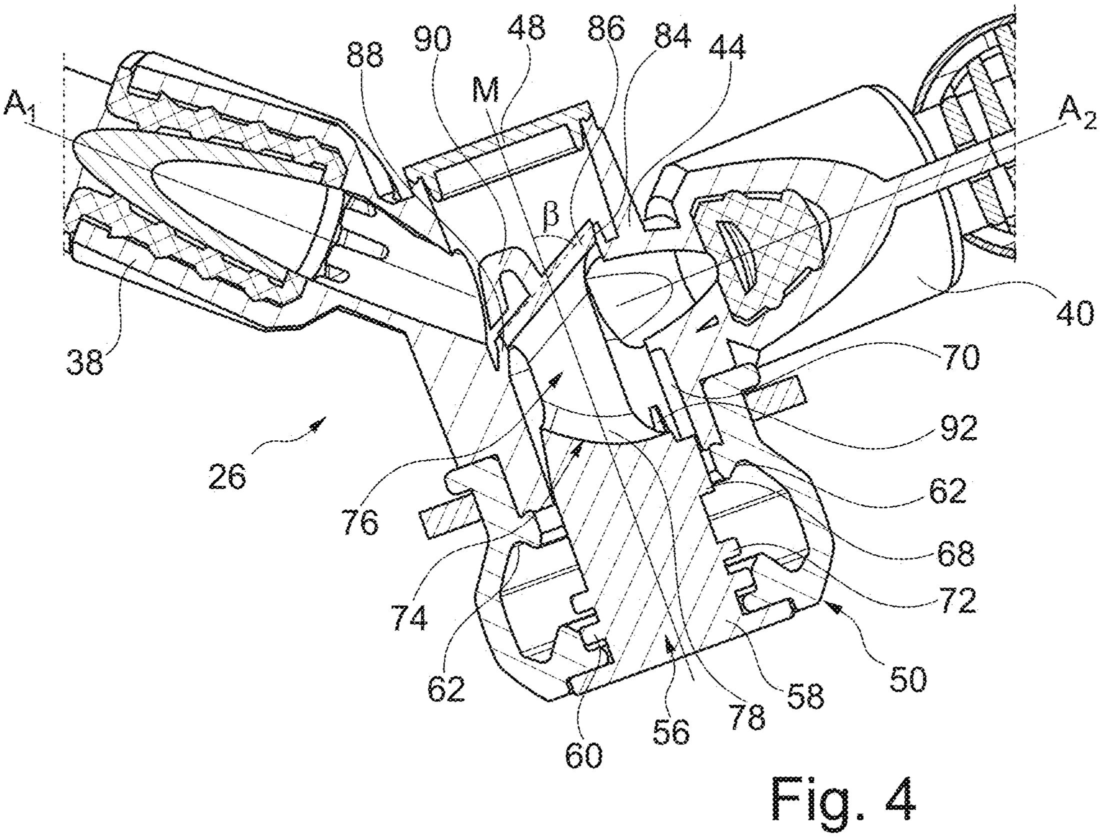
FIG. 4 shows the suction valve in a closed state in a sectional view.
Figure 5:
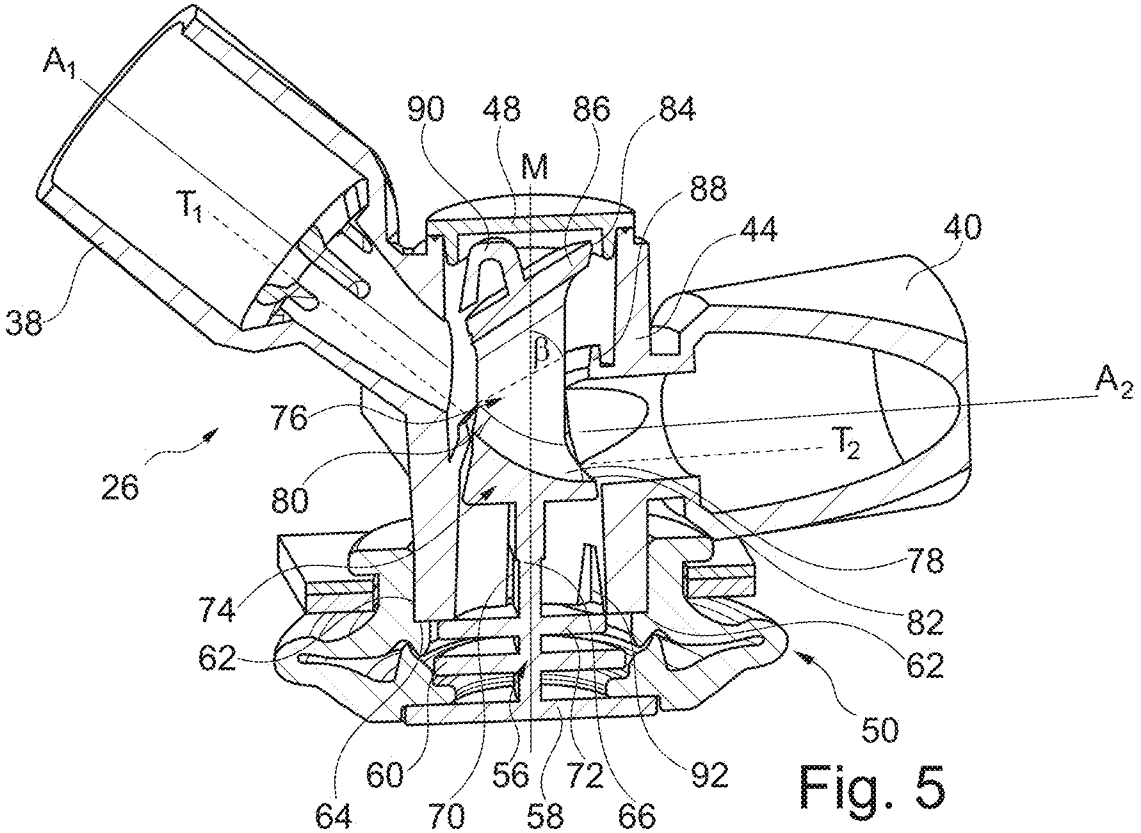
FIG. 5 shows the suction valve in an open state in a sectional view.
Figure 6:
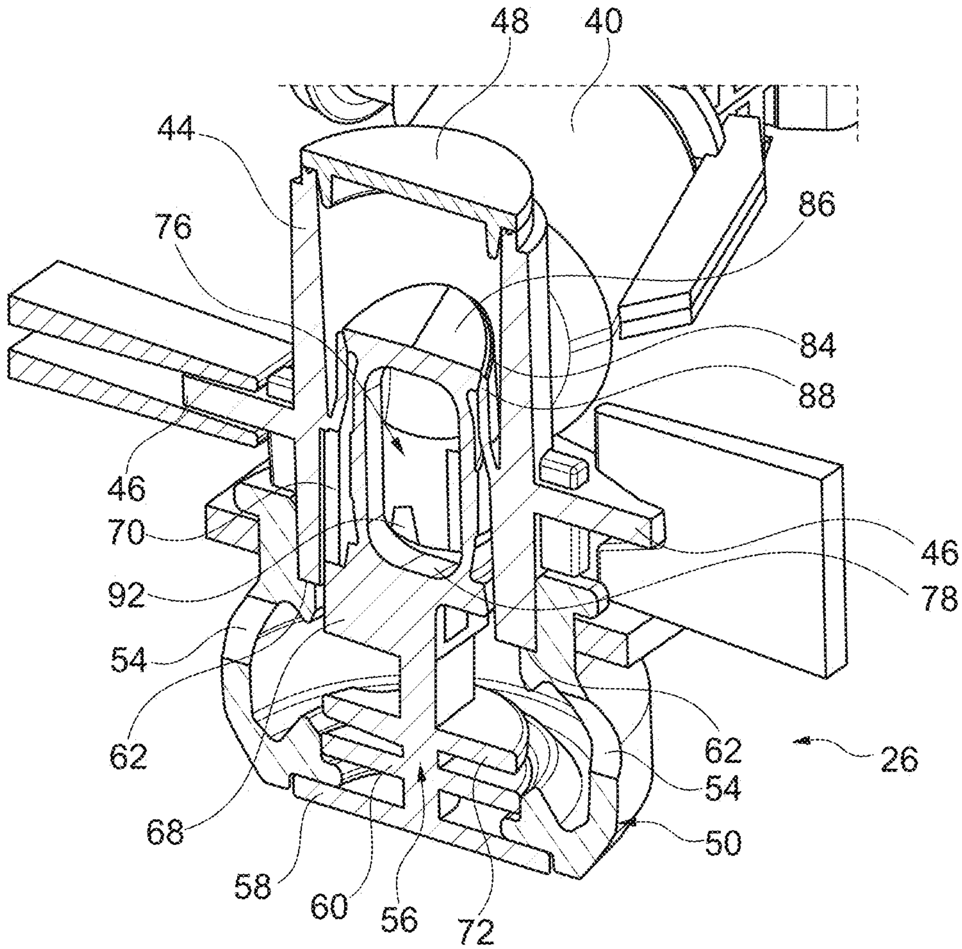
FIG. 6 shows the suction valve in the closed state in a sectional perspective view.

The internal structure of the suction valve 26 is explained below with reference to FIGS. 4, 5 and 6. FIGS. 4 and 6 show sectional views of the suction valve 26 in a closed state. FIG. 5 shows a sectional view of the suction valve 26 in an open state.

A stem 56 is arranged in the valve cylinder 44 of the suction valve 26. The stem 56 is configured to be axially displaceable or movable in the valve cylinder 44 along an axial direction or a center axis M of the valve cylinder 44, thereby opening and closing the suction valve 26. Specifically, the stem 56 includes a button portion 58. The button portion 58 is the portion of the stem 56 that protrudes furthest from the housing of the handle 4 and forms a planar pushing portion oriented normal to the longitudinal extension or axial direction of the stem 56 and is configured to be pushed by an operator to move the stem 56 along the axial direction or center axis M in the valve cylinder 44. The button portion 58 is surrounded by the valve spring 50 in a circumferential direction. The button portion 58 and the valve spring 50 form the suction button 28 protruding from the handle 4.

A detent portion 60 is formed adjacent to the button portion 58. The button portion 58 and the detent portion 60 are formed to receive a clamping edge 62 of the valve spring 50 between them. The valve spring 50 is made of an elastomeric material and therefore clamps between the button portion 58 and the detent portion 60. The detent portion 60 is substantially rib-shaped and extends, parallel to the button portion 58, in a direction radially outward with respect to the axial direction of the stem 56. At an end of the valve spring 50 facing away from the button portion 58, that is a connection section 62 of the valve spring 50 facing the valve cylinder 44, the valve spring 50 radially surrounds the valve cylinder 44. Here, the valve spring 50 clamps tightly onto the valve cylinder 44 due to its elastic properties. The valve spring 50 is formed with a circumferential sealing protrusion 64 that circumferentially contacts and seals an opening edge of the valve cylinder 44.

The stem 56 comprises a shaft portion 66 that extends from the button portion 58 into the valve cylinder 44. The shaft portion 66 has a substantially plate-like shape.

Guide pins 68 are formed in a width direction of the shaft portion 66, that slide in grooves 70 formed in an inner wall of the valve cylinder 44 to prevent rotation of the stem 56 relative to the valve cylinder 44. Furthermore, a stop 72 is formed on the shaft portion 66. The stop 72 is oriented parallel to the button portion 58 and the detent portion 60 and prevents overpressing of the stem 56 relative to the valve body 42. The stop 72, like the detent portion 60, is formed as a type of rib. Here, overpressing means that a portion of the stem 56 facing away from the button portion 58 is pressed against or comes into contact with the end cap 48.

Further, the stem 56 includes a piston portion 74. The piston portion 74 is formed at an end of the shaft portion 66 opposed to the button portion 58. The piston portion 74 comprises a through hole 76. The through hole 76 penetrates the piston portion 74 substantially in a direction normal or perpendicular to the axial direction of the stem 56. The through hole 76 is provided and configured to connect the inlet 38 and the outlet 40 of the suction valve 26 in an activated state of the suction valve 26 (shown in FIG. 5).

The through hole 76 comprises a curved flow guide 78 on or as a wall portion, specifically on the wall portion or wall surface oriented toward the button portion 58. The curved flow guide 78 is configured to redirect the flow from the inlet 38 to the outlet 40 as uniformly as possible. The curved flow guide 78 has no edges within a surface of the curved flow guide 78 and a substantially uniform curvature or a uniformly changing curvature. FIG. 5 shows in particular that in the valve open state the inlet 38, the outlet 40 and the curved flow guide 78 of the stem 56 are arranged and adapted to each other so as to provide a curved sideways flow path for the fluid and the mucus through the suction valve 26.

At a first edge 80 of the curved flow guide 78 facing the inlet 38, the curvature of the curved flow guide 78 is such that a first tangent T1 of the curved flow guide 78 is oriented parallel to the first center axis A1. At a second edge 82 of the curved flow guide 78 facing the outlet 40, the curvature of the curved flow guide 78 is such that a second tangent T2 of the curved flow guide 78 is oriented parallel to the second center axis A2.

The piston portion 74 further includes a circumferential sealing edge 84 formed on a sealing plate 86 that forms an end portion of the stem 56 away from the button portion 58 and bounds the through hole 76. The sealing plate 86 is configured to shut off the flow through the suction valve 26. Specifically, the sealing plate 86 is configured to be seated in a valve seat 88 in the closed state of the suction valve 26, with the sealing edge 84 sealing against the valve seat 88.

The valve seat 88 is formed in the valve cylinder 44. In particular, the valve seat 88 is formed integrally with the valve cylinder 44 from the same material. The valve seat 88 and thus also the sealing plate 86 with the sealing edge 84 are oriented inclined to the axial direction or center axis M. A second angle β, which is formed between the valve seat 88 and the center axis M, is smaller than 90°. The valve seat 88 is elastic. This means that the valve seat 88 can be expanded in an elastic manner and then elastically returns to its predetermined shape. The valve seat 88 and the sealing plate 86, having the sealing edge 84, are formed from the same material. In other words, the sealing between the valve seat 88 and the sealing edge 84 is a seal between identical materials, in particular plastics, preferably polypropylene. The sealing plate 86 is pressed into the valve seat 88 with a preloaded force. In other words, the valve spring 50 is preloaded in the closed state of the suction valve 26 shown in FIG. 4, so that the valve spring 50 presses the sealing plate 86 with the sealing edge 84 into the valve seat 88 with the preload force and keeps the suction valve 26 closed in the closed state, that is, in a state in which the suction valve 26 is not operated by the operator.

A retention hook 90 is formed on a surface of the sealing plate 86 facing away from the through hole 76. The retention hook 90 is formed as a resilient barb, which prevents the stem 56 from being pulled out from the valve cylinder 44. Specifically, the retention hook 90 latches onto the valve seat 88 when the sealing edge 84 of the sealing plate 86 overcomes the valve seat 88.

Figure 7:
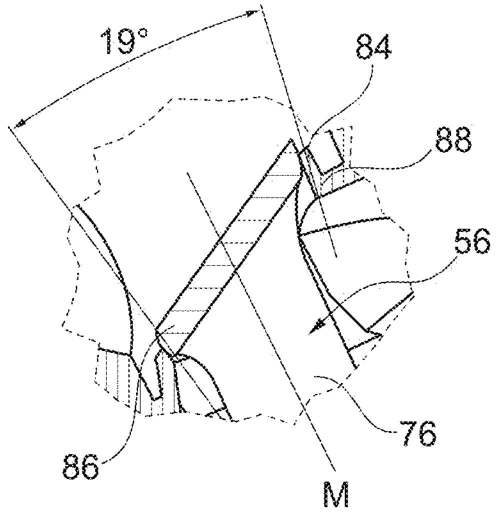
FIG. 7 shows a valve seat of the suction valve in the closed state in an enlarged view.

FIG. 7 shows an enlarged view of the sealing plate 86 in the valve seat 88. Both the valve seat 88 and the sealing edge 84 taper in a direction towards the through hole 76. In other words, the valve seat 88 and the sealing edge 84 are a conical valve seat 88 and a conical sealing edge 84, which are inclined at a third angle, the third angle being preferably 19°, to increase the sealing effect of the suction valve 26. 19° are to be understood here as an example. Of course, other angles are also possible.

In the following, the function of the suction valve 26 is briefly described with reference to the figures.

The suction pump P is connected to the vacuum port 32 via the hose 34 and generates a vacuum/suction force at the outlet 40. The suction valve 26 is in the closed state shown in FIG. 4. In other words, the sealing plate 86 with the sealing edge 84 is seated in the valve seat 88 of the valve cylinder 44 by the preload force applied by the valve spring 50. In the closed state of the suction valve 26, the suction pump P draws in air from the environment. This air is sucked into the suction valve 26 from the environment through the bypass holes 54 in the valve spring 50 and reaches the outlet 40 via bypass channels 92, which are formed in the inner wall of the valve cylinder 44. This effectively prevents the suction pump P from working against a big resistance in a closed state of the suction valve 26, which could damage the suction pump P and/or the endoscope 2.

Now, when the operator starts the suction function of the endoscope 2, that is, when the button portion 58 of the stem 56 is pressed hard enough by a finger of the operator to overcome the spring force of the valve spring 50, the stem 56 slides or moves in the valve cylinder 44. The stem 56 is guided in the grooves 70 via the pins 68. In this process, the sealing plate 86 with the sealing edge 84 leaves the valve seat 88 and opens the through hole 76. Specifically, the through hole 76 is axially displaced with the stem 56 in the valve cylinder 44 such that the through hole 76 now connects the outlet 40 to the inlet 38 of the suction valve 26. The suction force of the suction pump P can be transmitted to the working channel 14 via the suction channel 30 and fluid and mucus of the patient can be sucked off or aspirated. In the suction valve 26, the fluid and mucus is only deflected once through the curved flow guide 78, so that clogging of the suction valve 26 can be prevented. The fluid and mucus are diverted as evenly and gently as possible through the curved flow guide 78. The defined angle between inlet 38 and outlet 40 can further reduce the risk of clogging and enable gentle diversion through the curved flow guide 78.

Pressing the button portion 58 folds the valve spring 50 like a bellows (see FIG. 5). Two inner sections of the valve spring 50 come into contact in such a way that they lie sealingly on top of each other and close off the bypass holes 54. The stop 72 gives the operator a secure feeling that the suction valve 26 is fully open. In addition, the stop 72 prevents overpressing, so that the operator can press the button portion 58 fully without risk and without thinking.

When the operator wants to interrupt or stop the suction, he simply releases the button portion 58 and the spring force of the valve spring 50 moves the stem 56 axially through the valve cylinder 44 until the sealing plate 86 with the sealing edge 84 is seated again in the valve seat 88 and the suction valve 26 is closed. This automatically stops the elastic valve spring 50 from folding and opens the bypass holes 54 so that the suction pump P sucks in ambient air.

The following items are further variations and examples of the embodiments described with reference to the figures.

1. An endoscope (2) comprising: a proximal handle (4) or interface; an insertion cord (6) extending from the handle (4) or interface and configured to be inserted into a patient's body cavity; a working channel (14) configured to let fluid and/or mucus sucked from the patient's body cavity flow therethrough; the handle (4) or interface comprising: a suction valve (26) configured to control a suction through the working channel (14) and having a valve closed state and a valve open state; the suction valve (26) comprising: a valve body (42) having: a valve cylinder (44); an inlet (38) connected to the working channel (14); and an outlet (40) provided and configured to be connected to a suction device (P); and a stem (56) movable axially in the valve cylinder (44) between at least a first position, in which the suction valve (26) is in the valve closed state, and a second position, in which the suction valve (26) is in the valve open state; wherein the inlet (38) is connected to and extends away from the valve cylinder (44), the outlet (40) is connected to and extends away from the valve cylinder (44), the stem (56) comprises a curved flow guide (78), and the inlet (38), the outlet (40) and the curved flow guide (78) are arranged and adapted to each other so as to provide a curved sideways flow path for the fluid and/or mucus through the suction valve (26) in the valve open state.

2. The endoscope (2) according to item 1, wherein the curved sideways flow path is provided by the curved flow guide (78) of the stem (56) in combination with an enclosed angle (α) between a first orientation or center axis (A1) of the inlet (38) and a second orientation or center axis (A2) of the outlet (40) being larger than 90° and smaller than 180° seen in a side view of the handle (4) or interface in an assembled state of the suction valve (26) into the handle (4) or interface.

3. The endoscope (2) according to item 1 or 2, wherein the valve body (42) of the suction valve (26) comprises a valve seat (88) which is configured to make circumferential contact with a sealing edge (84) of the stem (56) in the valve closed state of the suction valve (26), thereby blocking a flow of fluid and mucus from the inlet (38) to the outlet (40).

4 The endoscope (2) according to item 3, wherein the valve seat (88) of the valve body (42) and the sealing edge (84) of the stem (56) are tapered at an acute angle in order to form a substantially conical sealing seat.

5. The endoscope (2) according to item 3 or 4, wherein the stem (56) comprises a sealing plate (86), the sealing plate (86) being formed at an end portion of the stem (56), the sealing plate (86) having the sealing edge (84) on an outer edge surrounding the sealing plate (86).

6. The endoscope (2) according to any one of the preceding items 3 to 5, wherein the stem (56) comprises a retention hook (90), which when the stem (56) is assembled into the valve body (42) can be pushed through the valve seat (88), and which when the stem (56) is pulled in a disassembly direction opposite an assembly direction hooks onto the valve seat (88), thereby preventing the stem (56) from being pulled out of the valve body (42).

7. The endoscope (2) according to any one of items 3 to 6, wherein the valve seat (88) of the valve body (42) is made of an elastic material or is elastically mounted therefore allowing the stem (56) to be assembled into the valve body (42) in a push-through manner.

8. The endoscope (2) according to any one of items 1 to 7, wherein the suction valve (26) comprises a valve spring, the valve spring being formed between the valve body (42) and the stem (56), the valve spring being configured to push the stem (56) to the first position, in which the suction valve (26) is in the valve closed state, wherein the valve spring has at least one bypass hole (54), which in the valve closed state allows ambient air to be drawn through the suction valve (26).

9. The endoscope (2) according to item 8, wherein the valve spring (50) is configured to form a bellows shape in a compressed state of the valve spring (50), thereby closing the bypass hole (54).

10. The endoscope (2) according to any one of items 1 to 9, wherein the stem (56) comprises a stop (72), which is configured to be brought into contact with the valve body (42) and prevents overpressing of the stem (56).

11. The endoscope (2) according to any one of items 1 to 10, wherein the stem (56) comprises a recess (76) the recess (76) extending, at least in sections, perpendicular to an axial direction of the stem (56), wherein the recess (76) in the valve open state connects the input (38) and the output (40 to each other and wherein the recess (76) comprises the curved flow guide (78).

12. The endoscope (2) according to any one of items 1 to 11, wherein the valve body (42) and the stem (56) are each formed in one piece from a thermoplastic material, preferably polypropylene.

13. The endoscope (2) according to item 12, wherein the proximal handle (4) comprises polypropylene, preferably consists essentially of polypropylene, and/or comprises at least 70% polypropylene. In one example, the two housing shells of the housing of the handle have an average wall thickness of 2.5 mm or less, preferably 2.0+/−0.2 mm. In one example, more than 70% of the wall of each housing shell has a wall thickness of 2.5 mm or less, preferably 2.0+/−0.2 mm.

14. The endoscope (2) according to item 12, wherein the proximal handle (4) comprises polypropylene, preferably consists essentially of polypropylene, and/or comprises at least 70% polypropylene, said propylene comprising at least 20% bio-polypropylene.

15. The endoscope (2) according to items 13 or 14, wherein the proximal handle (4) comprises two housing shells assembled with snap-fit shell fasteners without adhesives.

16. The endoscope (2) according to item 15, wherein the proximal handle (4) comprises press-fit component fasteners securing components of the endoscope within the shell without adhesives.

17. A method of assembling a suction valve (26) of an endoscope (2) according to any one of items 1 to 16, the suction valve (26) comprising a valve body (42), a stem (56) and a valve spring (50), the valve body (42) having an elastic valve seat (88), the method comprising the steps of: Attaching the valve spring (50) to the stem (56); Pushing the stem (56) into the valve body (42); Elastically bending the valve seat (88) of the valve body (42) with the stem (56); and Positioning the valve spring (50) on the valve body (42).

18. The method according to item 13, wherein the stem (56) comprises a retention hook (90) and the method further comprises the step of Passing a retention hook (90) of the stem (56) through the valve seat (88); after the step of pushing the stem (56) into the valve body (42).

19. A system comprising an endoscope (2) according to one of items 1 to 12 and a video processing apparatus (VPA).

LIST OF REFERENCE NUMBERS

2 endoscope
4 handle
6 insertion cord
8 insertion tube
10 bending section
12 distal tip unit
14 working channel
16 working channel access port
18 working channel tube
20 operating unit
22 Y-connector
24 connecting cable
24*a* electrical connector
26 suction valve
28 suction button
30 suction channel
32 vacuum port
34 hose
36 half-shell
38 inlet
40 outlet
42 valve body
44 valve cylinder
46 fixing projections
48 end cap
50 valve spring
52 side surface
54 bypass hole
56 stem
58 button portion
60 detent portion
62 clamping edge
64 sealing protrusion
66 shaft portion
68 guide pin
70 groove/slot
72 stop
74 piston portion
76 through hole
78 curved flow guide
80 first edge
82 second edge
84 sealing edge
86 sealing plate
88 valve seat
90 retention hook
92 bypass channel
T1 first tangent
T2 second tangent
M center axis of the valve cylinder
α first angle
β second angle
A1 first center axis
A2 second center axis
P suction pump
VPA video processing apparatus

We claim:

1. An endoscope comprising:

a handle or interface including a suction valve configured to control a suction;

an insertion cord extending distally from the handle or interface and configured to be inserted into a patient; and a working channel extending through the insertion cord and configured to let fluids suctioned from the patient flow therethrough, the suction valve being configured to control the suction through the working channel and comprising:

a valve body including a valve cylinder;

an inlet connected to the working channel, the inlet also connected to and extending away from the valve cylinder;

an outlet adapted to be connected to a suction device, the outlet also connected to and extending away from the valve cylinder;

a stem comprising a curved flow guide and being movable axially in the valve cylinder between at least a first position, in which the suction valve is in a valve closed state, and a second position, in which the suction valve is in a valve open state, the stem being configured to guide the fluid from the inlet to the outlet in the valve open state; and a valve spring positioned between the valve body and the stem and configured to close the suction valve, the valve spring comprising a bypass hole configured to allow ambient air to be drawn through the suction valve in the valve closed state, wherein the inlet, the outlet and the curved flow guide are configured to provide a curved sideways flow path for the fluid through the suction valve in the valve open state, and wherein, in a compressed state, the valve spring forms a bellows shape configured to close the bypass hole.

2. The endoscope of claim 1, wherein the curved sideways flow path is provided by the curved flow guide of the stem in combination with an enclosed angle, between a first orientation or center axis of the inlet and a second orientation or center axis of the outlet, being larger than 90° and smaller than 180° seen in a side view of the handle or interface in an assembled state.

3. The endoscope of claim 1, wherein the curved sideways flow path is provided by the curved flow guide of the stem in combination with an enclosed angle, between a first orientation or center axis of the inlet and a second orientation or center axis of the outlet, being larger than 90° and smaller than 180° seen in a side view of the handle or interface in an assembled state, wherein the stem comprises a sealing edge, and wherein the valve body comprises a valve seat configured to make circumferential contact with the sealing edge of the stem in the valve closed state.

4. The endoscope of claim 1, wherein the stem comprises a sealing edge, and wherein the valve body comprises a valve seat configured to make circumferential contact with the sealing edge of the stem in the valve closed state.

5. The endoscope of claim 4, wherein the valve seat and the sealing edge are tapered at an acute angle, the valve seat forming a substantially conical sealing seat.

6. The endoscope of claim 4, wherein the valve seat and the sealing edge are tapered at an acute angle forming a substantially conical seal in the valve closed state.

7. The endoscope of claim 4, wherein the stem comprises, at an end portion thereof, a sealing plate surrounded by the sealing edge.

8. The endoscope of claim 4, wherein the stem comprises a retention hook sized and configured to be pushed in a first direction through the valve seat and into the valve body during assembly, and wherein the retention hook is sized and configured to hook onto the valve seat when the stem is pulled in a direction opposite the first direction to prevent removal of the stem from the valve body.

9. The endoscope of claim 8, wherein the valve seat is elastic and configured to allow the stem to be assembled into the valve body in a push-through manner.

10. The endoscope of claim 1, wherein the curved sideways flow path is provided by the curved flow guide of the stem in combination with an enclosed angle, between a first orientation or center axis of the inlet and a second orientation or center axis of the outlet, being larger than 90° and smaller than 180° seen in a side view of the handle or interface in an assembled state, wherein the stem comprises a sealing plate surrounded by a sealing edge, wherein the valve body comprises a valve seat, and wherein the valve seat and the sealing edge are tapered at an acute angle forming a substantially conical seal in the valve closed state.

11. The endoscope of claim 10, wherein the stem comprises a retention hook sized and configured to be pushed in a first direction through the valve seat and into the valve body during assembly, and wherein the retention hook is sized and configured to hook onto the valve seat when the stem is pulled in a direction opposite the first direction to prevent removal of the stem from the valve body.

12. The endoscope of claim 11, wherein the valve seat is elastic and configured to allow the stem to be assembled into the valve body in a push-through manner.

13. The endoscope of claim 1, wherein the stem comprises a stop configured to contact the valve body and thus prevent overpressing of the stem.

14. The endoscope of claim 1, wherein the curved sideways flow path is provided by the curved flow guide of the stem in combination with an enclosed angle, between a first orientation or center axis of the inlet and a second orientation or center axis of the outlet, being larger than 90° and smaller than 180° seen in a side view of the handle or interface in an assembled state, wherein the stem comprises a stop and a sealing plate surrounded by a sealing edge, wherein the valve body comprises a valve seat, wherein the valve seat and the sealing edge are tapered at an acute angle forming a substantially conical seal in the valve closed state, and wherein the stop of the step is configured to be brought into contact with the valve body to limit motion of the stem.

15. The endoscope of claim 14, wherein the stem comprises a recess comprising the curved flow guide, the recess extending, at least in sections, perpendicular to an axial direction of the stem, and wherein the recess in the valve open state connects the inlet and the outlet to each other.

16. The endoscope of claim 1, wherein the stem comprises a recess comprising the curved flow guide, the recess extending, at least in sections, perpendicular to an axial direction of the stem, and wherein the recess in the valve open state connects the inlet and the outlet to each other.

17. The endoscope of claim 1, wherein the valve body and the stem are each comprised in one piece of a thermoplastic material comprising at least 70% polypropylene.

18. The endoscope of claim 1, wherein the handle, the valve body and the stem, are each comprised of at least 70% polypropylene material.

19. The endoscope of claim 18, wherein at least 20% of the polypropylene material is bio-propylene.

20. A system comprising the endoscope of claim 1 and a video processing apparatus.

* * * * *